United States Patent
Bonafini, Jr.

(10) Patent No.: US 9,669,135 B2
(45) Date of Patent: Jun. 6, 2017

(54) MIXED-PHASE BIOMATERIALS

(71) Applicant: Proton Innovations, LLC, Rochester, NY (US)

(72) Inventor: James A. Bonafini, Jr., Kendall, NY (US)

(73) Assignee: Proton Innovations, LLC, Rochester, NY (US)

( * ) Notice: Subject to any disclaimer, the term of this patent is extended or adjusted under 35 U.S.C. 154(b) by 0 days.

(21) Appl. No.: 14/813,814

(22) Filed: Jul. 30, 2015

(65) Prior Publication Data
US 2016/0030641 A1 Feb. 4, 2016

Related U.S. Application Data

(60) Provisional application No. 62/031,373, filed on Jul. 31, 2014.

(51) Int. Cl.
*A61L 29/06* (2006.01)
*A61L 29/16* (2006.01)
(Continued)

(52) U.S. Cl.
CPC ............. *A61L 29/06* (2013.01); *A61L 29/16* (2013.01); *C08G 18/3206* (2013.01);
(Continued)

(58) Field of Classification Search
CPC .... C08G 18/63; C08G 18/631; C08G 18/632; C08G 18/638; C08G 18/6564; A61L 29/049
(Continued)

(56) References Cited

U.S. PATENT DOCUMENTS 3,383,351 A   5/1968 Stamberger
4,000,218 A * 12/1976 Critchfield ......... C08G 18/0871
                                                      524/848
(Continued)

FOREIGN PATENT DOCUMENTS

CA    735010    5/1966
GB    1063222   3/1967

OTHER PUBLICATIONS

Andrew L. Hook, et al. Combinatorial discovery of polymers resistant to bacterial attachment. Nature Biotechnology. vol. 30, No. 9, Sep. 2012. p. 868-875.
(Continued)

*Primary Examiner* — Mike M Dollinger
(74) *Attorney, Agent, or Firm* — Woods Oviatt Gilman LLP; Katherine H. McGuire, Esq.; Douglas R. Smith, Esq.

(57) ABSTRACT

A method of preparing a mixed-phase thermoplastic biomaterial comprises contacting and reacting a diol and a graft pre-polymer comprising a diol and at least one covalently bonded unsaturated monomer with an organic diisocyanate compound. The reaction is conducted within an aprotic solvent and for a period of time and at a temperature sufficient to produce the mixed-phase thermoplastic biomaterial. The diol may be selected from the group consisting of siloxane diols, polyether diols, polyester diols and polycarbonate diols while the at least one covalently bonded unsaturated monomer may be selected from the group consisting of a fluorinated monomer, a siloxane monomer, an aliphatic ester of methacrylic acid, a cyclic ester of methacrylic acid, a charged monomer, a sulfonium salt, a vinyl monomer with phenol or benzoic acid, N-vinyl pyrrolidone, an aminoglucoside, and a therapeutic agent. The mixed-phase thermoplastic biomaterial may further include an anti-microbial, a therapeutic agent or both.

16 Claims, 7 Drawing Sheets

(51) Int. Cl.
*C08G 18/63* (2006.01)
*C08G 18/65* (2006.01)
*C08G 18/76* (2006.01)
*C08G 18/32* (2006.01)
*A61M 25/00* (2006.01)

(52) U.S. Cl.
CPC ....... *C08G 18/638* (2013.01); *C08G 18/6564* (2013.01); *C08G 18/7671* (2013.01); *A61L 2300/404* (2013.01); *A61M 25/0017* (2013.01)

(58) Field of Classification Search
USPC ......................................................... 525/454
See application file for complete search history.

(56) References Cited

U.S. PATENT DOCUMENTS

| | | | | |
|---|---|---|---|---|
| 5,034,461 A | * | 7/1991 | Lai | C08F 299/06 523/106 |
| 5,100,992 A | * | 3/1992 | Cohn | A61K 47/48176 424/501 |
| 5,428,123 A | * | 6/1995 | Ward | A61L 27/18 210/500.21 |
| 5,589,563 A | * | 12/1996 | Ward | A61L 27/18 210/500.21 |
| 2003/0216486 A1 | * | 11/2003 | Kawamoto | C08F 2/06 521/50 |
| 2010/0168356 A1 | * | 7/2010 | Lai | A61L 27/16 526/239 |
| 2013/0172592 A1 | * | 7/2013 | Li | C08G 18/61 556/419 |
| 2015/0065675 A1 | * | 3/2015 | Keaton | C08G 18/6564 528/53 |

OTHER PUBLICATIONS

Andrew L. Hook, et al. Discovery of Novel Material with Broad Resistance to Bacterial Attachment Using Combinatorial Polymer Microarrays. Avdanced Materials 2013,23,2542-2547.

* cited by examiner

__US 9,669,135 B2__

MIXED-PHASE BIOMATERIALS

TECHNICAL FIELD

The present invention relates to biomaterials, and more particularly to biomaterials having tunable bulk and surface properties, and even more particularly to biomaterials that may be fabricated to be biocompatible, anti-microbial and bio-erodible.

BACKGROUND OF THE INVENTION

Polymeric materials are used as catheters in many clinical situations every day. Typical materials such as medical grade silicone elicit a lower immunogenic response than previously used materials (polyurethanes or polyethylenes). Even with this development, silicone catheters have significant complications during acute and chronic use. These include biofilm formation, encrustation and bacterial infection.

In 2009, roughly 40% of infections acquired in U.S. hospitals were caused by urinary catheters, costing the healthcare system over $1 billion. Central venous catheters are estimated to cause roughly 80,000 bloodstream infections, resulting in 28,000 deaths and costing up to $2.3 billion annually. The most common pathogens to induce an infection include gram-positive *staphylococcus aureus* and *staphylococcus epidermidis*, as well as gram-negative *Escherichia coli* and *pseudomonas aeruginosa*. Bacteria can come from a variety of sources, including the operating room atmosphere, surgical equipment, clothing from medical staff, and even bacteria on the patient's skin and already in their body. Therefore, even under sterilized conditions, it can be difficult to prevent infections. In addition to infections, long term urinary catheterization increases the likelihood of encrustation, which is the buildup of minerals on the catheter and can potentially lead to urinary blockage.

The mechanism for bacterial adhesion onto a catheter occurs via a three step process: 1-2 hours after implantation, non-specific and reversible bonding occurs through gravitational, van der Waals, electrostatic, hydrogen bond, dipole-dipole, ionic bond, and hydrophobic interactions; roughly 2-3 hours later, stronger adhesion occurs via specific chemical interactions between the bacteria and substrate surface, forming irreversible bonds; and finally, if sufficient nutrients are supplied, a biofilm can form on the implant surface. Once a biofilm forms, roughly 1,000 times the antibiotic dose is required to treat the infection compared to killing the bacteria in suspension. In addition to infections, long term catheterization increases the likelihood of encrustation, which is the buildup of minerals on the catheter and can potentially lead to urinary blockage. For these reasons, there is a high interest in developing catheter materials that prevent bacterial and mineral adhesion.

The Foley catheter, which is the most commonly used device for urinary catheterization, is often made of silicone materials due to its low immunological response. A lubricious coating is often added in order to reduce urethral irritation. To address the issues of infections, some catheters are being coated with antimicrobial agents such as silver alloys or nitrofurazone. While antimicrobial coatings may cost up to twice as much as an uncoated catheter, their higher costs are becoming justified due to their ability to reduce infection rates, which can cost between $3,700 and $56,000 per patient. Despite the antimicrobial coatings' ability to reduce medical costs and infection rates compared to uncoated catheters, they are still not completely effective against preventing infections. One drawback is that most antimicrobial agents are not effective against all pathogens, especially antibiotic-resistant bacteria. In addition, antimicrobial coatings are not always effective against preventing biofilm formation for long-term catheterization. Even though antimicrobial coatings may kill the initial bacteria they interact with, the dead bacteria will still stick to the catheter, providing a perfect layer for new bacterial attachment and biofilm formation. Finally, in areas where the coating has been delaminated and the underlying catheter is exposed, bacteria can adhere very quickly since current catheter materials do not have an innate ability to prevent bacterial adhesion. For all these reasons, the likelihood of a catheter induced infection is directly correlated to the duration of catheterization, with the chances of infection increasing 3-10% daily.

To mitigate these problems, many patients have turned to intermittent catheters, which are disposable catheters and are used each time the bladder is emptied. Revenues for intermittent catheters were $143 million in 2009. While the chance for infection is greatly reduced, patients must be highly trained to use intermittent catheters since they can potentially cause urethra problems due to irritation. They are also expensive since they need to be replaced often.

SUMMARY OF THE INVENTION

The present invention addresses the above needs by providing a material having a chemical structure that exhibits surface properties which result in a discontinuous surface and a self-adjusting (smart) polymer configuration. This material may exhibit bio-erosion which removes any adhered materials and/or may also prevent biofilm formation that leads to a foreign body response. Since the material has a self-adjusting/heterogeneous surface, immunological response components do not recognize the biomaterial surface. Hydrophilic micro-domains in the biomaterial also contribute to the adjusting surface properties of the biomaterial depending on the surrounding environment.

The surface properties of the material of the present invention result from both the surface and bulk polymeric structure which is formed during the manufacturing process. These systems are based on those used in the manufacture of rigid contact lenses and flexible intra-ocular lenses which have proven to be biocompatible and possess properties which inhibit protein deposition and other adverse contaminations. The polymer material of the present invention generally comprises a base polymer which may be modified to incorporate a surface active agent or a grafted polymer moiety. The material may further include the addition of one or more interfacial agent polymer components and/or therapeutic agents.

In accordance with an aspect of the present invention, the base polymer layer consists of biocompatible synthetic polymer systems which have a hydrophilic/hydrophobic profile to facilitate surface dynamics, including a balanced hydrophilic/hydrophobic profile to facilitate drug retention/delivery. The base polymer further has thermoplastic properties amenable to extrusion processing into tubing or coatings. The base polymer is tunable to specific system requirements and may include derivatization of the polymer to include amino acids, proteins, anti-bacterial and bio-erodible agents, as well as other desired chemical properties. The base polymer is generally comprised of a polyurethane produced through the reaction of a diisocyanate with chemical moieties such as siloxane diols and organic polyols, and preferably organic diols. In accordance with a further aspect of the present invention, the organic diols may be modified through a pre-polymer reaction to produce grafted polymers with mixed-phases. These grafted pre-polymer building blocks have the desired diol terminal groups while also possessing one or more additional reaction sites within the polymer chain. These reactive pre-polymers can then be modified to include additional functional moieties, such as anti-adhesive compounds, anti-microbial agents and/or therapeutic compounds before being incorporated within the polyurethane-based biomaterial.

In an embodiment of the present invention, a method of preparing a polyurethane-based mixed-phase thermoplastic biomaterial comprises contacting and reacting a diol selected from the group consisting of siloxane diols, polyether diols, polyester diols and polycarbonate diols with a graft pre-polymer and an organic diisocyanate compound, wherein the graft pre-polymer comprises a diol and at least one covalently bonded unsaturated monomer selected from the group consisting of a fluorinated monomer, a siloxane monomer, a zwitterionic monomer such as but not limited to an amino acid, phosphorycholine and the like, an aliphatic ester of methacrylic acid, a cyclic ester of methacrylic acid, a charged monomer, a sulfonium salt, a vinyl monomer with phenol or benzoic acid, N-vinyl pyrrolidone, an aminoglucoside, and a therapeutic agent. The reaction is conducted within an aprotic solvent and for a period of time and at a temperature sufficient to produce the mixed-phase thermoplastic biomaterial.

In a further embodiment of the present invention, the method further includes contacting and reacting an interfacial agent. The interfacial agent comprises a) a solvatable constituent which is solvatable within the aprotic solvent but not compatible with the diol and b) a non-solvatable constituent which is compatible with the diol but not solvatable within the aprotic solvent.

DETAILED DESCRIPTION

The manufacturing process used to develop the biomaterials in accordance with the present invention is based upon reverse phase polymerization. An exemplary process is described within U.S. Pat. No. 4,000,218 to Critchfield et al. issued Dec. 28, 1976. Reversed phase polymerization has been shown to produce polymers in particulate form and in high purity as required for use in medical devices. As part of the process, it is necessary to use and/or synthesize interfacial agents specifically suited for the system. The interfacial agent generally includes a diol terminated polymer chain having at least one reactive site within the chain. In accordance with a further aspect of the invention, the interfacial agent may be modified to incorporate a zwitterionic moiety such as an amino acid or phosporylcholine and derivatives thereof. An aliphatic species, preferably a saturated hydrocarbon, is chemically bonded to the reactive site. In this manner, the interfacial agent possesses a hydrophilic domain which may be incorporated within the bulk polyurethane base polymer while also having a hydrophobic tail extending outwardly from the base polymer. As a result, when the reaction materials (i.e. the polyurethane precursors, such as methylene diphenyl diisocyanate and an organic diol, and the interfacial agent) are placed within an aprotic solvent such as hexane, benzene or toluene, reverse micelles are formed. As a result, these interfacial agents serve a dual purpose: a) to suspend particles in process in the aprotic solvent and b) to modify the surface characteristics of the resultant polyurethane material.

Figure 1:
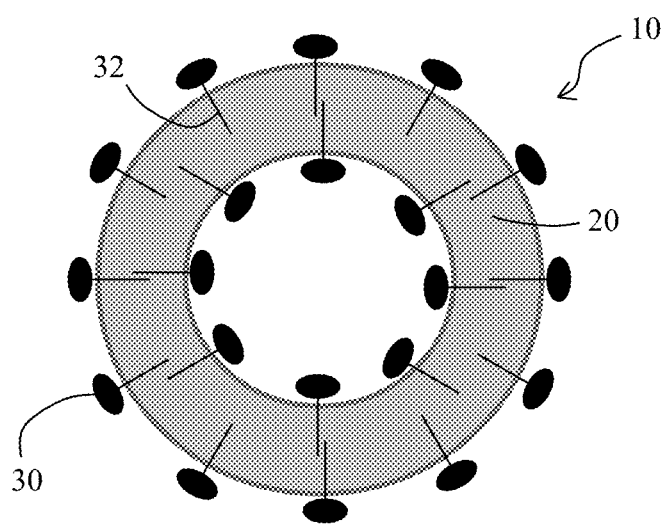
FIG. 1 is a schematic cross-section of an embodiment of a catheter comprised of a biomaterial in accordance with an embodiment of the present invention.
Figure 2:
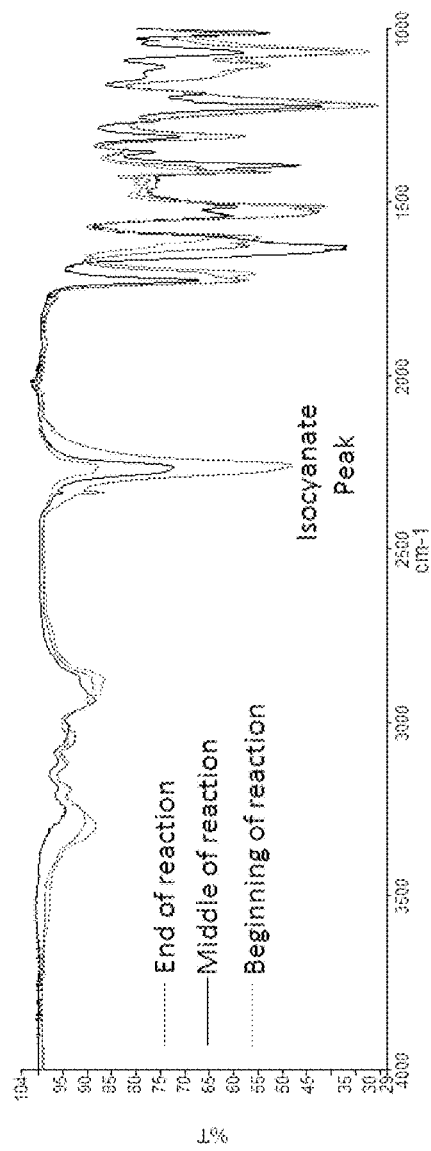
FIG. 2 is an overlay of multiple FTIR spectra showing reduction of the isocyanate peak as the polyurethane reaction progresses.

For example, as shown in FIG. 1, medical device 10 (such as a urinary catheter) is generally comprised of a base polymer 20. In accordance with an aspect of the present invention, base polymer 20 is a polyurethane composed of polymerized diisocyanate/diol. The diisocyanate has a general formula O=C=N—R—N=C=O, where R is either an aliphatic chain, such as hexamethylene diisocyanate (HDI), or is aromatic such as toluene diisocyanate (TDI) or methylene diphenyl diisocyanate (MDI). The diol may be a siloxane diol or an organic diol, such as but not limited to polyethylene glycol (PEG), tetraethylene glycol, 1,4-butane diol, a lactone diol such as poly(caprolactone) diol or a polycarbonate diol. To monitor the progression of the polyurethane reaction, Fourier transform infrared (FTIR) spectroscopy may be used to interrogate isocyanate consumption. Consumption of the isocyanate groups indicates extension of the polymer backbone and the attachment of graft pre-polymers (discussed below). The isocyanate may also be monitored since specific amounts of unreacted isocyanate groups may be desired to remain on the polymer in order to improve adhesion between the substrate (i.e. medical device 10) and a coating later of the biomaterial of the present invention. Alternatively, unreacted isocyanate groups may also be further derivatized following the polyurethane formation reaction by quenching the reaction with a solution containing one or more zwitter ions such as amino acids or amino acid analogs. In this manner, the polyurethane backbone may be modified to increase its biocompatibility and/or increase its functionality via the additional reaction site on the zwitter ion. An overlay of exemplary FTIR spectra tracking polyurethane reaction progression is shown in FIG. 2.

Figure 3:
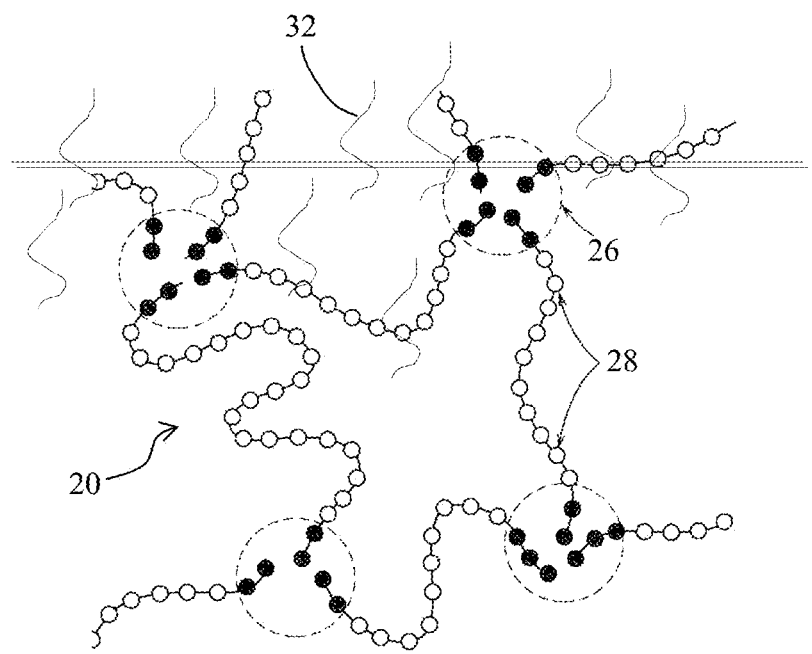
FIG. 3 is a schematic structural view of a polymeric biomaterial in accordance with the present invention.
Figure 4:
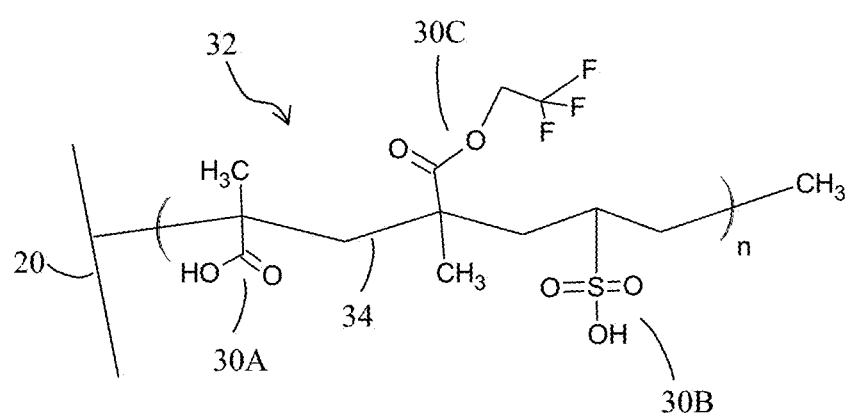
FIG. 4 is an exemplary schematic of a graft polymer suitable for use within a polymeric biomaterial in accordance with the present invention.

In accordance with an aspect of the present invention, partially embedded within base polymer 20 are one or more surface active agents 30 (see also FIG. 3). Surface active agents 30 may be covalently bonded to the diol backbone of the polyurethane base polymer 20. Alternatively and/or additionally, surface active agents 30 may also be incorporated within the base polymer 20 via a graft pre-polymer 32 (see also FIG. 4) which will be discussed in greater detail below. In one aspect of the invention, surface active agents 30 are tailored to provide surface properties required for long term implants, such as catheters or other devices where long-term biocompatibility is desired.

Base polymer 20 exhibits the microstructure (hard-soft segments 26-28, FIG. 3) well known in polyurethanes. This microstructure is arranged in such a way so as to induce a synergistic effect with the surface active agent 30. The micro-domains present within the base polymer 20 play a role in both the mechanical and surface properties of the final devices. These domains are dictated by the feed composition in the polymer synthesis and manipulated by the thermal history and ultimate manufacturing technique employed when fabricating the polyurethane polymer.

Surface active agents 30 may be incorporated within the polyurethane base polymer 20 during polymerization of the polyurethane or may be later reactively added through suitable chemical reactions to functional groups located on the base polymer 20. For example, U.S. Pat. No. 3,383,351 to Stamberger issued May 14, 1968, discloses a pre-polymer grafting polymerization pre-processing step before the polyurethane polymerization reaction. That is, in accordance with an aspect of the present invention, the diol grafted pre-polymer 32 employed within the polyurethane polymerization has been pre-processed so as to become derivatized to either include the surface active agent 30 or to include a reactive site for later functionalization of the polyurethane base polymer 20 (see FIG. 4). The grafted pre-polymer 32 also allows for compositional control of the polyurethane base polymer which further modifies both the base polymer 20 and the surface properties of the surface active agents 30.

With continued reference to FIG. 3, surface active agents 30A-30C may be unsaturated monomers covalently integrated within backbone 34 of pre-polymer 32. Examples of such surface active agents may include charged monomers such as methacrylic acid 30A and vinyl sulfonic acid 30C, and an anti-adhesive fluorinated monomer 30B such as 2,2,2-trifluoroethyl methacrylate. Additional surface active agents may include, without limitation, aliphatic methacrylates, fluoromethacrylates, sulfonium salts, vinyl monomers with phenol or benzoic acid, N-vinyl pyrrolidone, a zwitterionic monomer such as but not limited to an amino acid, phosphorycholine and the like, and functionalized aminoglucosides.

The grafted pre-polymer creates a mixed-phase polymeric structure enabling the fine tuning of the surface properties of medical device 10. In one aspect of the present invention wherein medical device 10 is fabricated directly from the mixed-phase biomaterial, the bulk properties of medical device 10 are dictated by the polyurethane structure of base polymer 20 and include both rheological properties and micro-domains within the polymer. Tuning of the polyurethane reaction materials and synthesis produces bulk polymers suitable for melt processing into tubing and other shapes, as well as for the application of coatings from appropriate solvents. In a further aspect of the present invention, the mixed-phase biomaterial may be surface coated onto a pre-fabricated medical device, such as already commercially available urinary catheters. In either case, the local surface characteristics of the medical device may be modified according to the proposed end-use of the medical device and may include anti-adhesive and/or anti-microbial properties, or may include covalently bonded therapeutic agents for site specific and/or time released application. Derivatization of the surface may be through complimentary functional groups on the polyurethane polymer main chain or through the grafted pre-polymers.

For instance, antimicrobial polymers may be produced by attaching or inserting an active microbial agent onto either the polyurethane or a graft pre-polymer backbone via an alkyl or acetyl linker. In accordance with one aspect of the present invention, graft pre-polymer 32 is specifically chosen for its enhanced antimicrobial properties. Examples of such antimicrobial moieties include, but are not limited to vinyl monomers with phenol or benzoic acid, functionalized aminoglucosides, charged monomers such as methacrylic acid, vinyl sulfonic acid, and sulfonium salts, and fluorinated monomers.

Figure 5:
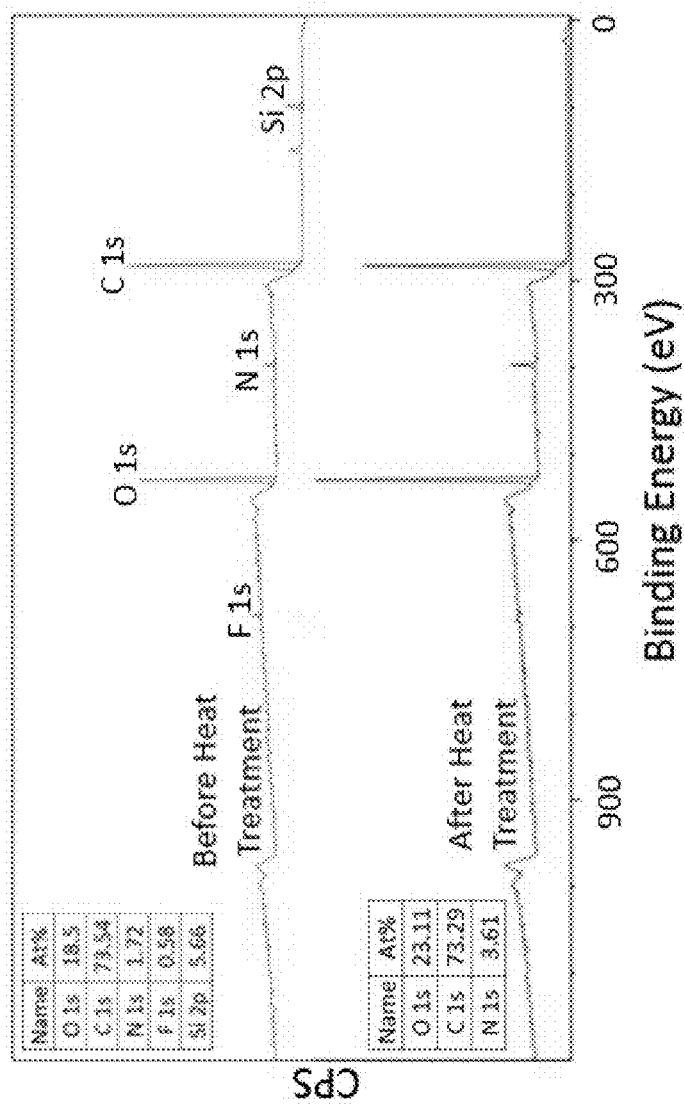
FIG. 5 are XPS spectra of an exemplary mixed-phase polymer before and after heating for 3 hours at 80° C.

In accordance with a further aspect of the present invention, the mixed-phase biomaterial may reduce bacterial adhesion due to the biomaterial's non-uniform and self-adjusting surface which is non-conducive for bacterial attachment since bacteria prefer unchanging and predictable surfaces when forming biofilms. The polymers synthesized using an embodiment of the manufacturing process of the present invention have non-uniform and dynamic surface chemistries due to variation of the material's surface composition from the graft pre-polymers 32. Graft pre-polymers 32 also create hydrophillic/hydrophobic and positively/negatively charged microdomains within the resultant biomaterial. The material's composition and micro-domains are dictated by the feed composition, solvent, reaction conditions, and post-treatment procedures such as thermal annealing and washing. By way of example, X-ray photoelectron spectroscopy (XPS), such as the results shown in FIG. 5 for a mixed-phase material including graft pre-polymers having silicon and fluorine substituted methacrylates, may verify that heat treatment at 80° C. for three hours can alter the surface chemistry so that the fluorine and silicon groups of the representative material no longer appear on the surface.

Figures 6A, 6B:
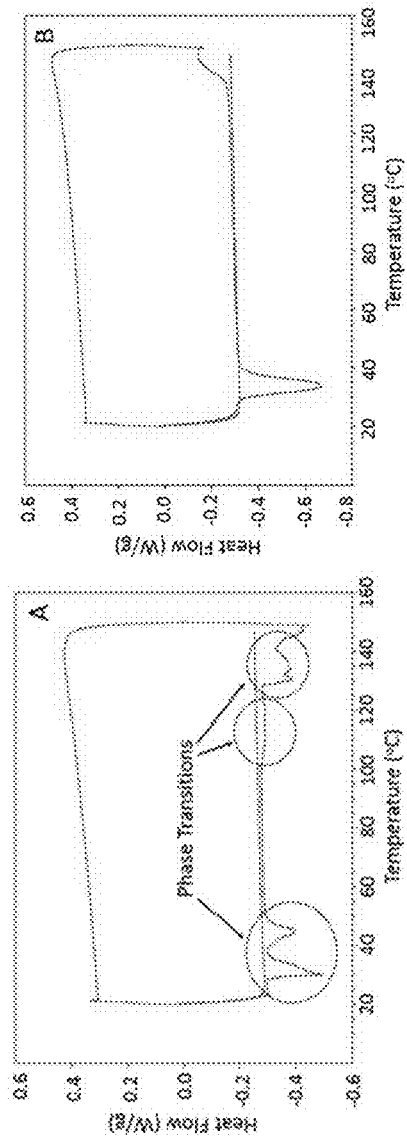
FIGS. 6A and 6B are comparative DSC thermograms of A) an exemplary mixed-phase polymer and B) an ungrafted polymer.

The self-adjusting nature of the biomaterial surface may also be demonstrated by its ability to be dissolved in both hydrocarbon and aprotic polar solvents. Limited solubility of the biomaterial is seen in alcohols and the biomaterial is not soluble in water, although slight surface hydration is seen because of the dynamic nature of the surface. Information on miscibility and polymer-to-polymer interactions can be revealed through the use of differential scanning calorimetry (DSC). As seen in FIG. 6A, a representative biomaterial consists of multiple phases due to graft pre-polymer (side-chain) composition. The graft pre-polymer influences the biomaterial's final properties. As can be seen in FIG. 6A, the representative biomaterial includes one or more components (such as graft pre-polymers and/or surface active agents) which are thermo-responsive and lead to multiple phase transitions. It can be seen that one phase transition is at or near body temperature (37° C.), which decreases the surface modulus and contributes to the biomaterial's self-adjusting surface properties at a biologically relevant temperature. As a comparison, FIG. 6B shows an ungrafted polymer, which contains only a single phase transition.

Figure 7:
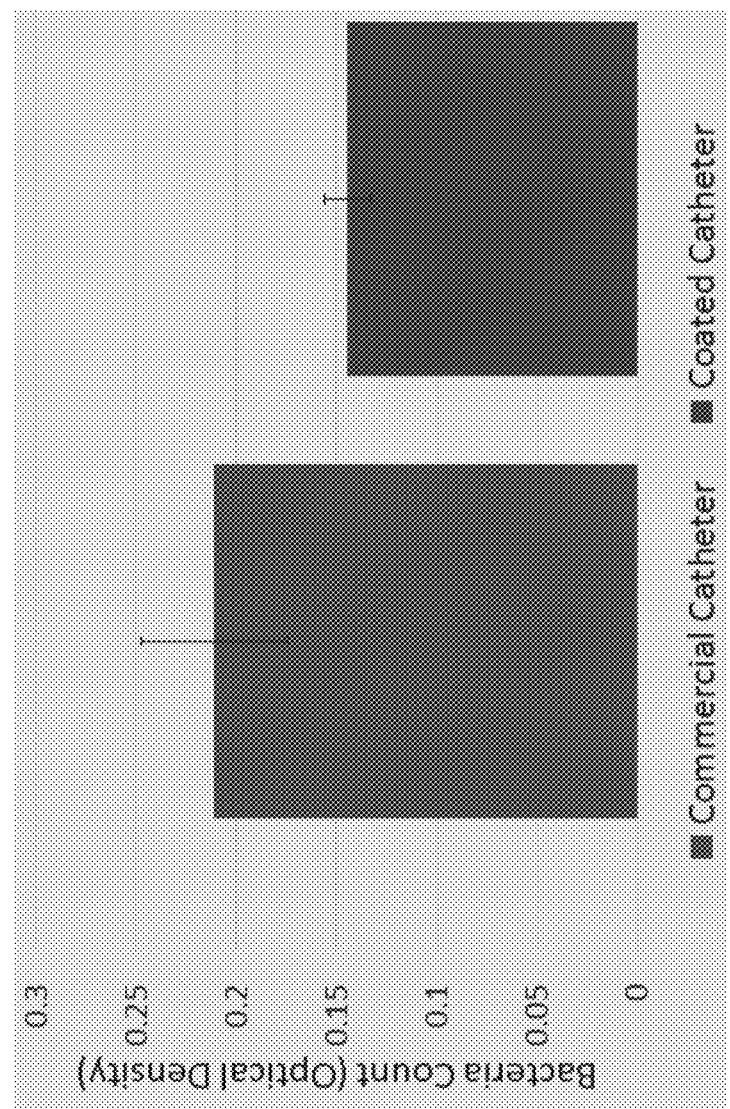
FIG. 7 is a plot of a bacterial count on a commercial catheter and a catheter coated with an exemplary mixed-phase polymer showing reduced bacterial adhesion on the coated catheter.

An example of the improved bacterial anti-adhesion properties of the biomaterials of the present invention over commercial catheters is shown in FIG. 7. Commercial catheters, with and without biomaterial coatings, were placed into a suspension of *Staphylococcus aureus* bacteria for 24 hours. After staining and removing the bacteria on the catheters, the bacteria were quantified using ultra-violet spectroscopy. The number of bacteria counted was averaged over 5 samples of each catheter type (whether with or without a biomaterial coating). FIG. 7 shows that an exemplary biomaterial coating produced in accordance with the present invention exhibits a 33% reduction in bacterial adhesion compared to an uncoated commercially available catheter.

The following examples are illustrative of the present invention and not to be regarded as limitative thereto.

Example 1

Preparation of Methacrylate End-Capped Poly(Caprolactone) Diol

In a reaction vessel, hydroxyethyl methacrylate, 1.0 g, caprolactone, 60 g, and 0.1 g stannous octoate were added and mixed until homogeneous. The solution was heated to 82° C. overnight (16-24 hours). This resulted in a waxy solid.

Example 2

Preparation of Poly(Caprolactone) Diol

In a reaction vessel, tetraethylene glycol, 1.0 g, caprolactone, 60 g and 0.1 g stannous octoate were added and mixed until homogeneous. The solution was heated to 82° C. overnight (16-24 hours). This resulted in a waxy solid.

Example 3

Preparation of Graft Polymer a

In a reaction vessel, the following were added:

| Component | Amount (g) |
| --- | --- |
| PEG-1000 | 150 |
| N-vinyl pyrrolidone | 1.0 |
| Methyl methacrylate | 10 |
| Lauryl methacrylate | 7.9 |
| Tris | 2.1 |
| Benzoyl peroxide | 0.12 | where Tris is 3-[Tris(trimethylsiloxy)silyl]propyl methacrylate.

The solution was heated from 70° C. to 100° C. while mixing with an overhead mechanical agitator. After 3 hours the solution was cooled and 20 g of dimethyl acetamide was added to decrease viscosity of the polymer solution.

Example 4

Preparation of Graft Polymer B

In a reaction vessel, the following were added:

| Component | Amount (g) |
| --- | --- |
| PEG-1000 | 90 |
| N-vinyl pyrrolidone | 2.8 |
| Methyl methacrylate | 4.0 |
| Methacrylic acid | 1.0 |
| Lauryl methacrylate | 2.0 |
| Tris | 3.1 |
| Benzoyl peroxide | 0.04 | where Tris is 3-[Tris(trimethylsiloxy)silyl]propyl methacrylate.

The solution was heated at 70° C. for 48 hours. A viscous solution was recovered.

Example 5

Preparation of Graft Polymer C

In a pressure bottle, the following were added:

| Component | Amount (g) |
| --- | --- |
| PEG-1000 | 90 |
| N-vinyl pyrrolidone | 1.0 |
| Methyl methacrylate | 2.0 |
| Tetrafluoroethyl methacrylate | 1.65 |
| Lauryl methacrylate | 2.0 |
| Tris | 5.0 |
| AIBN | 0.024 | where Tris is 3-[Tris(trimethylsiloxy)silyl]propyl methacrylate.

The solution was heated at 70° C. for 48 hours in a mechanical convection oven. A viscous solution was recovered which formed into a waxy solid at room temperature.

Example 6

Preparation of Graft Polymer D

In a reaction vessel, the following were added:

| Component | Amount (g) |
| --- | --- |
| PEG-1000 | 90 |
| N-vinyl pyrrolidone | 2.8 |
| Methyl methacrylate | 1.0 |
| Isobornyl methacrylate | 3.0 |
| Methacrylic Acid | 1.0 |
| Lauryl methacrylate | 2.0 |
| Tris | 3.1 |
| Benzoyl peroxide | 0.04 | where Tris is 3-[Tris(trimethylsiloxy)silyl]propyl methacrylate.

The solution was heated at 70° C. for 48 hours in a mechanical convection oven. A viscous solution was recovered which formed into a waxy solid at room temperature.

Example 7

Preparation of Interfacial Agent a

In a pressure bottle, the following were added:

| Component | Amount (g) |
| --- | --- |
| Polycaprolactone of Example 1 | 98 |
| Lauryl methacrylate | 15.0 |
| Toluene | 30 |
| AIBN | 0.03 |

The solution was heated at 70° C. for 48 hours in a mechanical convection oven. A viscous solution was recovered. Interfacial agent is used in polyurethane reactions where polycaprolactone diols are used in aprotic hydrocarbon solvent systems.

Example 8

Preparation of Interfacial Agent B

In a pressure bottle, the following were added:

| Component | Amount (g) |
| --- | --- |
| Polycaprolactone of Example 1 | 98 |
| Styrene | 15.0 |
| Toluene | 30 |
| AIBN | 0.03 |

The solution was heated at 70° C. for 48 hours in a mechanical convection oven. A viscous solution was recovered. Interfacial agent is used in polyurethane reactions where polycaprolactone diols are used in aprotic hydrocarbon solvent systems.

Example 9

Preparation of Mixed-Phase Biomaterial a

Figure 8:
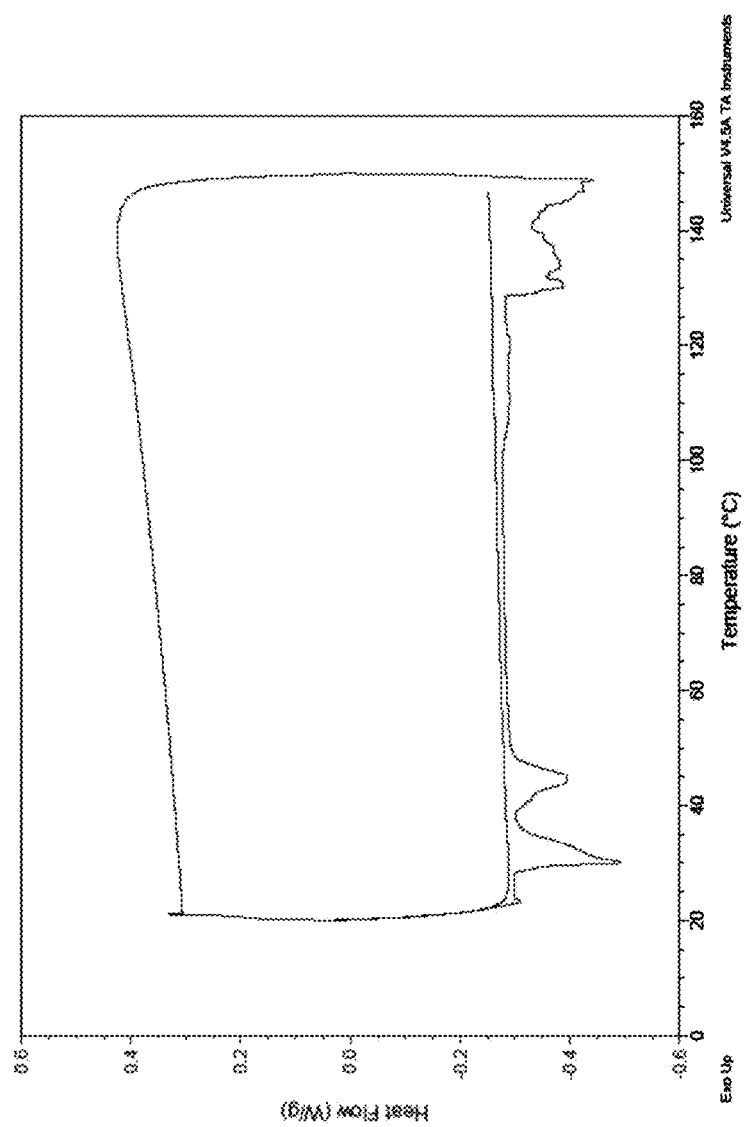
FIG. 8 is a DSC thermogram of an exemplary mixed phase biomaterial.

Toluene, 200 g was added to a jacketed reaction vessel equipped with overhead mechanical agitator. Brij S100 strearyl 10 g was added and mixed thoroughly. Once solubilized 26.2 g tetraethylene glycol, 3.3 g butane diol and 131.1 g of polymer graft from Example 3 were added. Methyl diphenyl diisocyanate (MDI) was melted and added to 30 g of toluene. The MDI solution was added to the reactor at room temperature under agitation and mixed until exotherm was exhausted. The solution was then heated to 80° C. for 2 hours until the viscosity reached 25 cps @ 50° C. as measured by a cone & plate Brookfield viscometer. The material was recovered by precipitation into hexane. As shown in FIG. 8, the material exhibited multiple phase transitions as measured by differential scanning calorimetry.

Example 10

Preparation of Mixed-Phase Biomaterial B

Toluene, 130 g was added to a jacketed reaction vessel equipped with overhead mechanical agitator. Brij S100 strearyl 7.2 g was added and mixed thoroughly. Once solubilized, 2.4 g butane diol and 90 g of polymer graft from Example 5 were added. Methyl diphenyl diisocyanate (MDI) 30 g was melted and was added to the reactor at room temperature under agitation. It was mixed until exotherm was exhausted. The solution was then heated to 90° C. for 2 hours until the viscosity reached 45 cps @ 50° C. as measured by a cone & plate Brookfield viscometer. The material was recovered by precipitation into hexane.

Example 11

Preparation of Methacrylate End-Capped Polycarbonate Diol

In a reaction vessel, hydroxyethyl methacrylate, 1.0 g, dimethyl carbonate, 10 g tetraethylene glycol (TEG), 10 g and 0.1 g potassium carbonate were added and mixed until homogeneous. The solution was heated to 85° C. overnight (16-24 hours) followed by 3-4 hours at 140° C. at which point the polymer was recovered. The preferred molecular weight of the methacrylate end-capped polycarbonate polymer was in the range of 1000 to 5000. Alternately a PEG of 1000 MW may be used instead of TEG to obtain higher MW functionalized diols.

Example 12

Preparation of Polycarbonate Diol

In a reaction vessel, dimethyl carbonate, 10 g tetraethylene glycol (TEG), 10 g and 0.1 g potassium carbonate were added and mixed until homogeneous. The solution was heated to 85° C. overnight (16-24 hours) followed by 3-4 hours at 140° C. at which point the polymeric diol was recovered. The preferred molecular weight of the diol was in the range of 1000 to 5000. Alternately a PEG of 1000 MW may be used instead of TEG to obtain higher MW diols.

Example 13

Polycarbonate/Polyurethane Biomaterial

Toluene, 130 g was added to a jacketed reaction vessel equipped with overhead mechanical agitator. Brij S100 strearyl 7.2 g was added and mixed thoroughly. Once solubilized, 2.4 g butane diol and 90 g of diol from Example 11 were added. Methyl diphenyl diisocyanate (MDI) 30 g was melted and was added to the reactor at room temperature under agitation. It was mixed until exotherm was exhausted. The solution was then heated to 90° C. for 2 hours until the viscosity was above 50 cps @ 50° C. as measured by a cone & plate Brookfield viscometer. The material was recovered by precipitation into hexane.

Although the invention has been described with reference to preferred embodiments thereof, it is understood that various modifications may be made thereto without departing from the full spirit and scope of the invention as defined by the claims which follow.

What is claimed is:

1. A method of preparing a polyurethane-based thermoplastic biomaterial which comprises contacting and reacting:
   a) a diol that is selected from the group consisting of siloxane diols, polyether diols, polyester diols and polycarbonate diols;
   b) a graft pre-polymer prepared from the reaction of polyethylene glycol with at least 3-[tris(trimethylsiloxy)silyl]propyl methacrylate; and
   c) an organic diisocyanate compound,
   the reaction being conducted within an aprotic solvent and for a period of time and at a temperature sufficient to produce the mixed-phase thermoplastic biomaterial.

2. The method of claim 1 further including contacting and reacting an interfacial agent, the interfacial agent comprising a) a solvatable constituent which is solvatable within the aprotic solvent but not compatible with diol and b) a non-solvatable constituent which is compatible with the diol but is not solvatable within the aprotic solvent.

3. The method of claim 1 wherein the thermoplastic biomaterial includes an anti-microbial, a therapeutic agent or both.

4. The method of claim 1 wherein the thermoplastic biomaterial includes at least one covalently bonded amino acid.

5. The method of claim 1 wherein the thermoplastic biomaterial exhibits multiple phase change transitions over the temperature range of about 20° C. and about 120° C.

6. The method of claim 5 wherein at least two of the multiple phase change transitions occurs in the temperature range of about 20° C. and about 70° C.

7. The method of claim 1 wherein the graft pre-polymer also contains a covalently bonded unsaturated monomer and the at least one covalently bonded unsaturated monomer is selected from the group consisting of a fluorinated monomer, a siloxane monomer, an aliphatic ester of methacrylic acid, a cyclic ester of methacrylic acid, a charged monomer, a sulfonium salt, a vinyl monomer with phenol or benzoic acid, N-vinyl pyrrolidone, an aminoglucoside, a zwitterionic monomer such as but not limited to an amino acid, phosphorycholine and the like, and a therapeutic agent.

8. A polyurethane-based thermoplastic biomaterial comprising the reaction product of:
   a) a diol that is selected from the group consisting of siloxane diols, polyether diols, polyester diols and polycarbonate diols;

b) a graft pre-polymer prepared from the reaction of polyethylene glycol with at least 3-[tris(trimethylsiloxy)silyl]propyl methacrylate;

c) an organic diisocyanate compound.

9. The polyurethane-based thermoplastic biomaterial of claim 8 wherein the biomaterial is produced through a reaction being conducted within an aprotic solvent.

10. The polyurethane-based thermoplastic biomaterial of claim 9 wherein the reaction proceeds for a period of time and at a temperature sufficient to produce the mixed-phase thermoplastic biomaterial.

11. The polyurethane-based thermoplastic biomaterial of claim 8 further comprising:

d) an interfacial agent comprising:
   i) a solvatable constituent which is solvatable within an aprotic solvent but not compatible with the diol and
   ii) a non-solvatable constituent which is compatible with the diol but is not solvatable within the aprotic solvent.

12. The polyurethane-based thermoplastic biomaterial of claim 8 further comprising:

d) an anti-microbial, a therapeutic agent or both.

13. The polyurethane-based thermoplastic biomaterial of claim 8 wherein the mixed-phase thermoplastic biomaterial includes at least one covalently bonded amino acid.

14. The polyurethane-based thermoplastic biomaterial of claim 8 wherein the thermoplastic biomaterial exhibits multiple phase change transitions over the temperature range of about 20° C. and about 120° C.

15. The polyurethane-based thermoplastic biomaterial of claim 14 wherein at least two of the multiple phase change transitions occur in the temperature range of about 20° C. to about 70° C.

16. The polyurethane-based thermoplastic biomaterial of claim 8 wherein the graft pre-polymer also contains a covalently bonded unsaturated monomer and the at least one covalently bonded unsaturated monomer is selected from the group consisting of a fluorinated monomer, a siloxane monomer, an aliphatic ester of methacrylic acid, a cyclic ester of methacrylic acid, a charged monomer, a sulfonium salt, a vinyl monomer with phenol or benzoic acid, N-vinyl pyrrolidone, an aminoglucoside, a zwitterionic monomer, and a therapeutic agent.

* * * * *